United States Patent [19]
Stickney et al.

[11] Patent Number: 6,147,273
[45] Date of Patent: Nov. 14, 2000

[54] METHOD FOR THE SEPARATION OF COMPOUNDS HAVING OLEFINIC UNSATURATION

[75] Inventors: Michael J. Stickney, Houston; Edward M. Jones, Jr., Friendswood; M. S. Chandrasekharaiah, Houston, all of Tex.

[73] Assignee: MC International Research, Houstin, Tex.

[21] Appl. No.: 09/119,436

[22] Filed: Jul. 20, 1998

[51] Int. Cl.$^7$ .................................. C07C 7/10; C07C 7/00
[52] U.S. Cl. ............................ 585/843; 585/844; 585/860
[58] Field of Search ..................................... 585/843, 844, 585/860

[56] References Cited

U.S. PATENT DOCUMENTS

| | | | |
|---|---|---|---|
| 1,977,659 | 10/1934 | Watts | 260/170 |
| 2,289,773 | 7/1942 | Gilliland | 260/677 |
| 2,498,204 | 2/1950 | Francis | 260/677 |
| 4,174,353 | 11/1979 | Marcinkowsky et al. | 585/835 |
| 4,328,382 | 5/1982 | Alter et al. | 585/844 |
| 4,430,205 | 2/1984 | Felsky | 208/246 |
| 5,057,641 | 10/1991 | Valus et al. | 585/818 |

OTHER PUBLICATIONS

"Selective Olefin Recovery," Richard Ranchas, Petrochemicals Spring 1997, pp. 117–122.

"Reaction of Olefins with Solid Cuprous Halides," by E. R. Gilliland, J.E. Seebold, J. B. FitzHugh, and P. S. Morgan, vol. 61, pp. 1960–1962 Aug. 1939.

"Thermodynamics of the formation of the Isobutene–Silver Ion Complex" A.N. Petron, O.N. Temkin, and M.I. Bogdanov; Russian Journal Physical Chemistry, 44(11), 1970. pp. 1574–1576.

"The Structure–Stability Relationship of the Metal Ion Complexes of Unsaturated Compounds. III; The Effects of Polar Substituents on the Silver Ion–Olefin Complexation." Takayuki Fueno, O. Kajimoto & Junji Furukawa. Bulletin of the Chemical Society of Japan. vol. 41–pp. 782–785 (1968).

"On the Ligand Exchange Equilibrium in the Propylene–Mercury (II) Complex, " I. Kaukii, R. Nakajima, & T. Hara, Bulletin of the Chemical Society of Japan, vol. 43, pp. 749–755 (1970).

"Thermodynamics of the Formation of a Silver Ion–Propene–Complex" A.N. Petron, O.N. Timpkin & M.I. Bogdanor, Russian Jouranl Physical Chemistry, 45(1), 1971, pp. 19–21.

"Coordination of Silver Ion with Unsaturated Compounds V. Ethylene and Propene," K. Trueblood & H.J. Lucas, Mar. 5, 1952.

"Solubility of Propylene in Aqueous Silver Nitrate, "I.H. Cho, D. L. Cho, H. K. Yasuda, & T.R. Maurade, J. Chem. Eng. Data 1995, 40, pp. 102–106.

"Separation of Ethylene from Ethane by Supported Liquid Membranes Containing Silver Nitrate as a Carrier," M. Teramoto, H. Matsuyama, T. Yamashiro, & Y Katayama. vol. 19, No. 5, 1986. pp. 419–424.

"Liquid Complexes of Lower Olefins with Anhydrous Metal Salts," by Alfred W. Francis, Oct. 19, 1950. pp. 3709–3715.

"The Coordination of Silver Ion with Unsaturated Compounds," by S. Winstein and H.J. Lucas, Apr., 1938, vol. 60, pp. 836–847.

*Primary Examiner*—Walter D. Griffin
*Assistant Examiner*—Tam M. Nguyen
*Attorney, Agent, or Firm*—Streets & Steele; Patrick K. Steele; Jeffrey L. Streets

[57] ABSTRACT

Olefins may be separated from paraffins, particularly those having the same number of carbon atoms, more easily than by fractional distillation by contacting a feed containing both materials with an aqueous solution of silver nitrate and nitric acid. The olefins form water soluble complexes with silver and are recovered by heating the water to decompose the complexes, thereby producing an olefin concentrate. In the absence of nitric acid contaminant hydrogen reduces the silver to metal and causes it to form colloidal solids and acetylenes form explosive solid compounds with silver. The nitric acid prevents the formation of insoluble solids by hydrogen and causes the silver acetylides to decompose during the olefin recovery step. Carrying out multiple stages of extraction and recovery can produce very high purity olefin.

49 Claims, 1 Drawing Sheet

METHOD FOR THE SEPARATION OF COMPOUNDS HAVING OLEFINIC UNSATURATION

BACKGROUND OF THE INVENTION

1. Field of the Invention

The present invention relates to the separation of compounds having olefinic unsaturation from other compounds by means of complexing the olefinically unsaturated compounds with transition metal salts, particularly silver salts, in aqueous solutions and liberating the olefinically unsaturated compounds by decomposing the complex. More particularly, the invention provides a means to prevent the formation of dangerous unstable metal acetylides.

2. Related Art

The separation of olefins from corresponding paraffin is difficult by the conventional methods of the prior art, e.g., lean oil extraction and/or fractional distillation.

It is known that several transition metals in the +1 valence state form moderately stable complexes with compounds having olefinic unsaturation. Among the transition metals which exhibit the property are silver, copper (+1), mercury (+1), rhodium (+2), palladium (+2) and platinum (+2). All of these metals with the exception of silver exhibit valences of +2 and may form very stable complexes in the +2 valence. Copper will form more stable complexes in the +2 valence state.

The commercial significance of separating compounds having olefinic unsaturation from other compounds using the complexing property of the transition metals depends on the ability to easily decompose the complexes and release the olefinic compound. The metals other than silver and copper are more expensive and their use in large quantities associated with this type of separation present prohibitive capital costs.

Silver, on the other hand, is of moderate cost and has only one valence state. The silver complexes are soluble in water whereas the remainder of the organic steam, mainly hydrocarbons, has only slight solubility in water. This is described in U.S. Pat. No. 4,328,382 issued May. 2, 1982. U.S. Pat. No. 4,174,353 issued Nov. 13, 1979, discloses the removal of silver acetylide in the aqueous silver nitrate solution with silver permanganate or ozone and $H_2O_2$ to control Ag precipitation.

Presently there is no commercial application of this technology for olefin separation.

"Selective Olefin Recovery", *Petrochemicals Technology Quarterly*, pages 117–122, Spring 1997, Barchas, describes a process for upgrading refinery-grade (about 70%) propylene to polymer-grade (99%+) propylene. In this process gaseous feed enters a packed section and is contacted with descending silver nitrate solution. A complex is formed between the silver and the olefin which is then dissolved in the aqueous solution to form a "rich" solution. The complex containing solution is then flashed by pressure letdown into a drum which releases the olefin. The article also describes a process using a gas permeable membrane, through which the olefin containing gas passes into a silver nitrate solution to form a silver complex in solution while the paraffin gases pass out unaffected.

Barchas particularly points out two substantial problems with his silver nitrate/olefin recovery process. The first is the presence of hydrogen in the olefin containing feed gas. Hydrogen reduces the silver salt and results in the precipitation of silver metal in the system. Barchas advises silver nitrate cannot be used unless the hydrogen is removed or silver somehow prevented from precipitation. However, no solution is offered.

The second problem is the formation of compounds of silver with some feed contaminants, namely diolefins, acetylenes, sulfides and chlorides. The solid sulfides and chlorides are an inconvenience and cause loss of available silver and must be removed by filtration. However, the article, although noting the hazard of solid silver acetylides, may be considered to understate the problem.

Silver acetylides are extremely unstable, particularly if they become dry. Thus, this solid material passing through the system, even if filtered out, may explode within the olefin plant. This is an extreme hazard, and in this format is not likely to result in any commercial use of the silver salts for olefin removal or recovery.

If these two primary problems can be eliminated, then the use of silver salts for selective olefin separation from saturated compounds would substantially reduce the cost of capitalization and operation from the prior commercial systems.

It is an advantage of the present invention that moderately stable silver complexes are formed with hydrocarbon mixtures including compounds having olefinic unsaturation. It is a particular advantage that compounds having olefinic unsaturation are easily separated from saturated compound having the same number of carbon atoms. It is a further advantage of the present process that silver is not reduced and precipitated by hydrogen present in the organic feed to the process. It is a particular advantage of the present process that unstable compounds of silver and acetylenes are not formed during the olefin separation process.

SUMMARY OF THE INVENTION

The present invention comprises contacting an aqueous solution of a transition metal salt, preferably a silver salt, more preferably silver nitrate, and an acid, preferably nitric acid, with an organic feed containing at least one compound containing an olefinic unsaturation under condition of temperature and pressure to form a complex of silver. Since the acid does not inhibit the complexing reaction, the presence of the acid gives the assurance that should either one or both, hydrogen or acetylenes, be present the reaction will not be adversely affected.

The olefins are recovered by separating the aqueous solution in which the silver complexes are dissolved, and heating the solution to decompose the complexes.

The acid redissolves the colloidal silver metal formed by hydrogen reduction and prevents the formation of the silver acetylides at the temperature employed in the regeneration of the olefin complex so that the olefin separation process is carried out in the presence of acetylenes without the formation or reformation of silver acetylides. Thus, according to the present invention neither silver permanganate nor ozone nor $H_2O_2$ is required during the process. The present process is preferably characterized as carried out in the absence of silver permanganate and $H_2O_2$.

DETAILED DESCRIPTION

Figure 1:
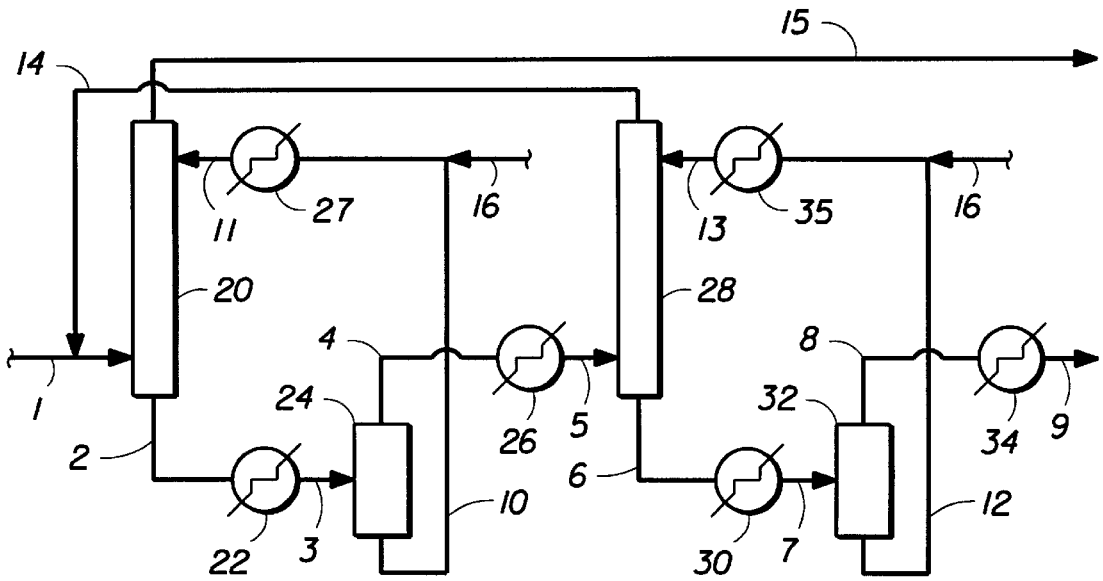
FIG. 1 is a schematic representation of a two stage olefin extraction and separation process according to the present invention.

Mixed refinery streams which would be a source of the feeds for the present process contain a broad spectrum of olefinic compounds. This is especially true of products from either catalytic cracking or thermal cracking processes. These unsaturated compounds comprise ethylene, acetylene, propylene, propadiene, methyl acetylene, butenes, butadiene, amylenes, hexenes etc. Many of these compounds are valuable, especially as feed stocks for chemical products. Ethylene and propylene especially are recovered with purities greater than 90%. Additionally, the butenes are recovered.

The acid, preferably nitric acid, may be present in the aqueous silver salt solution in any concentration, however, the presence of acid may reduce the solubility of the silver salt, thus the concentration of acid is preferably below 20 vol %, more preferably less than 10 vol % of the aqueous solution in the range of about 1 to about 10 vol %.

The transitions metal include metals of Group IB, IIB, VIIIB Table of Elements or mixtures thereof, preferably Ag, Cu, Hg, Rh, Pd, Pt or mixtures thereof and most preferably Ag.

The formation of metal, e.g. silver complexes with olefinic unsaturation (or greater unsaturation such as acetylinic unsaturation) is selective and any organic feed, preferably a hydrocarbon stream, containing at least one compound having an olefinic unsaturation may be used.

In one embodiment a gasoline stream containing $C_4$–$C_9$ hydrocarbons may be treated to remove olefins, diolefins, and acetylenes to improve its stability. The presence of the nitric acid causes the silver acetylides to not form or to decompose during the regeneration step for the olefins, thus the olefins, diolefins, and acetylenes are all recovered as a separate stream. The diolefins and acetylenes are usually only contaminants in the feeds being processed according to the present invention and may be well tolerated in the recovered olefins or may be mere nuisance impurities.

A preferred embodiment of the present invention is the separation of olefins from paraffinic (saturated compounds) having the same number of carbon atoms, e.g., ethylene/ethane, propylene/propane, butylenes/butanes and the like. In this preferred embodiment hydrocarbon feeds in the range of two to nine carbon atoms, preferably having 2 to 6 carbon atoms and preferably encompassing a single range of hydrocarbons, e.g., refinery cuts of predominately $C_2$, $C_3$, $C_4$ or $C_5$ hydrocarbons are employed with the silver salt to complex the olefins, solubilize the complex in an aqueous solution and remove the olefin from the corresponding paraffins. As noted above the more highly unsaturated compounds are also complexed and removed from the paraffins.

The olefins are recovered by heating the aqueous solution containing the complexed olefins to decompose the complex. The olefins are recovered and the silver salt reconstituted for recycle to the contact and complexing step. The decomposition will preferably be in the range of 140 to 300° F.

The acid which is useful in the present process is $HNO_3$

An interesting feature of the complex formation is that the salt need not be totally in solution. In a preferred embodiment for the operation of the present process, the silver salt is present in excess of its solubility in the aqueous system, preferably an excess of 5 to 25 wt. % beyond solubility. Preferably the excess is present as finely divided solid particles and may be transported in the liquid phase as a slurry. The advantage of the excess solid silver salt is that a given volume of silver salt contacting solution has a greater complexing capacity that the same solution without the solid silver salt, since the silver salt need not be in solution to form the complex. This reduces the energy needed to obtain a given level of complex formation compared to the prior art. Silver salts in excess of the amounts recited would be operable, however the excess solids may impose handling problems on the system.

In addition to silver nitrate a silver salt useful in the present invention include silver fluoride AgF.

The present process may be carried out in continuous or batch operations. In dealing with refinery streams and petrochemical plant operations, continuous processes are preferred. There may be substantial cost savings by performing a first stage separation at the refinery then transporting the olefins to a market hub where a second stage separation takes place producing, for example, a polymer grade propylene of 99.5% purity. The reactors are contemplated to be counterflow with the organic (hydrocarbon) feed moving upward through a packed bed and the aqueous extractant solution comprising the aqueous silver salt/nitric acid solution and silver olefin complex moving downward.

In the present extractions the organic feed may be either gaseous or liquid. The contacting may be conveniently carried out in a packed or trayed column such as those conventionally used for gas/liquid or liquid/liquid contact. The flow may be either concurrent or countercurrent. The pressure and temperature are adjusted to achieve the desired condition (liquid or gas) for the organic, e.g. hydrocarbon phase with the aqueous solution being in liquid phase. Since the olefin silver complex is heat sensitive, the temperature during the contacting to form the complex is maintained below the decomposition temperature, preferably below 100° F., more preferably below 90° F.

It has been observed that a single contacting stage achieves separation of olefin(s) from the other components in the feed. In order to achieve higher olefin purity, the recovered olefin concentrate is preferably contacted in a second stage to further remove the saturated hydrocarbons and concentrate the olefin to 99.50%. Even higher olefin purity may be obtained by a third stage of extraction and recovery.

The FIG. 1 illustrates a separation of propylene from propane. The feed is 25%/75% propane/propylene, which enters the first extractor 20 via line 1. This embodiment is operated as a liquid/liquid contact in countercurrent flow. The hydrocarbon feed passes up through a packed column. A silver nitrate solution, preferably at or exceeding the saturation point of the salt, and containing 1–10% nitric acid enters the column 20 via line 11 and passes down through the column which is operated at 200 psig and about 86° F.

Most or essentially all of the propylene forms the water soluble silver complex and a small amount of propane is also dissolved in the water phase which passes out through line 2 to heater 22 where it is heated to about 160° F. and passes via line 3 into flash drum 24. The silver propylene complex is decomposed along with any silver acetylides and released from the aqueous solution. The lean silver nitrate solution is recycled via line 10/11 to column 20 after being first cooled to around 86° F.

The propylene and dissolved propane (and any acetylenes) exit overhead though line 4 into heat exchanger 26 where it is cooled to around 86° F. prior to entry into the second stage extractor 28 which is also operated with a liquid/liquid counterflow contact at about 200 psig. The hydrocarbon feed again passes up through the column and a silver nitrate/nitric acid aqueous stream enters packed column 28 to flow downward and further extract the propylene while the propane enriched stream passes via line 14 to line 1 for recycle into the first stage extractor.

The propylene enriched stream from the second stage extractor 28 passes via line 6 through heat exchanger 30 where it is heated to 160° F. and passes in line 7 into flash drum 32. The high purity propylene passes out through line 8 and may be cooled in heat exchanger 34 before leaving the battery limits of the unit via line 9. The lean silver nitrate solution passes via line 12 through heat exchanger 35 for cooling prior to recycle to column 28 via line 13.

Make-up silver nitrate solution and/or nitric acid may be made via line 16. A slip stream (not shown) would normally be withdrawn from the silver nitrate recycle to remove insoluble impurities such as the sulfides or chlorides or other solids which may be present.

The table shows the composition of each stream in pounds per hour for the two stage extraction process. The recovered propylene is 99.5+%. The acetylenes, if any, are removed with the propylene. The presence of nitric acid prevents the reduction of the silver to metal by any hydrogen present.

In this schematic presentation, such items as pumps, reboilers, valves and the like have been omitted, but their location and operation would be readily apparent to the ordinary engineer.

TABLE

| Stream Flow (lb/hr) | 1 | 2 | 3 | 4 | 5 |
|---|---|---|---|---|---|
| PROPANE | 25000 | 5454.9 | 5454.9 | 4959 | 4959 |
| PROPYLENE | 75000 | 82050.1 | 82050.1 | 74591 | 74591 |
| $AgNO_3$ | 0 | 224137 | 224137 | 0 | 0 |
| $HNO_3$ | 2.5 | 12334 | 12334 | 2.0 | 2.0 |
| $H_2O$ | 40.0 | 188837 | 188837 | 31.8 | 31.8 |
| Total | 100043 | 512813 | 512813 | 79584 | 79584 |
| Temp (F.) | 120 | 120 | 160 | 160 | 120 |

| Stream Flow (lb/hr) | 6 | 7 | 8 | 9 | 10 |
|---|---|---|---|---|---|
| PROPANE | 391 | 391 | 352 | 352 | 496 |
| PROPYLENE | 77759 | 77759 | 69983 | 69983 | 7459 |
| $AgNO_3$ | 191174 | 191174 | 0 | 0 | 224137 |
| $HNO_3$ | 10520 | 10520 | 1.8 | 2 | 12332 |
| $H_2O$ | 161065 | 161065 | 28.1 | 28 | 188805 |
| Total | 440910 | 440910 | 70335 | 70365 | 433229 |
| Temp (F.) | 120 | 160 | 160 | 120 | 160 |

| Stream Flow (lb/hr) | 11 | 12 | 13 | 14 | 15 |
|---|---|---|---|---|---|
| PROPANE | 496 | 39 | 39 | 4607 | 20041 |
| PROPYLENE | 7459 | 7778 | 7776 | 4608 | 409 |
| $AgNO_3$ | 224137 | 191174 | 19174 | 0 | 0 |
| $HNO_3$ | 12332 | 10518 | 10518 | 0.2 | 105 |
| $H_2O$ | 18805 | 161037 | 161037 | 3.7 | 8.2 |
| Total | 433229 | 370545 | 370545 | 9219 | 20450 |
| Temp (F.) | 120 | 160 | 120 | 120 | 120 |

Figure 2:
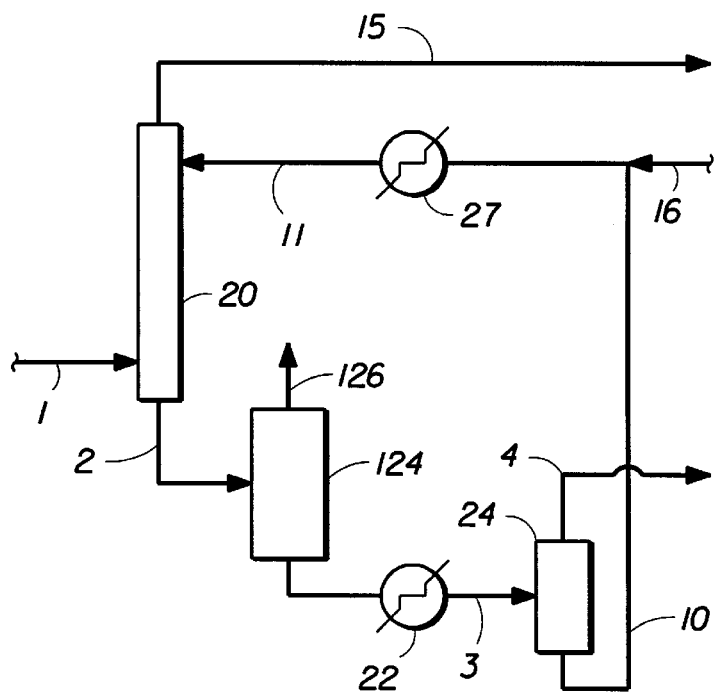
FIG. 2 is a schematic representation of a one stage olefin extraction and separation process according to the present invention.

FIG. 2 uses the same first stage as In FIG. 1 but use a vent column 124 under conditions of pressure and temperature to cause the alkane, e.g. propylene in a propylene purification to vaporize from the aqueous solution while maintaining the silver/propylene complex. The "rich" solution from column 20 passes via line 2 to vent column 124 operated at 160 psia and 80° F. A portion of the propane dissolved in the aqueous solution is flashed and vented through line 126. The aqueous solution is then passed through heater 22 into flash drum 24 from which the propylene at about 95% purity is recovered via line 4.

The invention claimed is:

1. A process comprising contacting an aqueous solution of a silver salt and nitric acid with an organic feed containing at least one compound containing an olefinic unsaturation having a first concentration under conditions of temperature and pressure to form a complex of said silver salt and said compound containing said olefinic unsaturation, wherein the silver salt is present in the aqueous solution in excess of its solubility as finely divided solid particles transported as a slurry, and wherein said contacting is in the absence of silver permanganate, ozone and hydrogen peroxide.

2. The process according to claim 1 wherein said organic feed comprises hydrocarbons having 2 to 9 carbon atoms.

3. The process according to claim 1 wherein said organic feed comprises hydrocarbons having 2 to 6 carbon atoms.

4. The process according to claim 2 wherein said hydrocarbons comprise olefins and paraffins of the same number of carbon atoms.

5. The process according to claim 2 wherein said complex of silver and the compound containing olefinic unsaturation is separated from said organic feed and decomposed to recover said compound having olefinic unsaturation in a second concentration greater than said first concentration.

6. The process according to claim 1 wherein said silver salt is silver nitrate.

7. The process according to claim 1 comprising:

contacting a feed comprising hydrocarbons having 2 to 9 carbon atoms and containing at least one olefin with the aqueous slurry, wherein the silver salt is silver nitrate, forming water soluble complexes of silver and olefin, removing said aqueous solution containing said silver complexes from contact with said hydrocarbons, decomposing said silver complexes and recovering said olefin.

8. The process according to claim 7 wherein nitric acid is present in the range of 0.5 to 10 wt. % of said solution.

9. The process according to claim 7 wherein said hydrocarbons comprise a mixture of olefins and paraffins having varying numbers of carbon atoms.

10. The process according to claim 7 wherein said olefins have varying numbers of carbon atoms.

11. The process according to claim 7 wherein hydrocarbons comprise olefins and paraffins having the same number of carbon atoms.

12. The process according to claim 11 wherein said hydrocarbons comprise ethylene and ethane.

13. The process according to claim 11 wherein said hydrocarbons comprise propylene and propane.

14. The process according to claim 11 wherein said hydrocarbons comprise butylenes and butanes.

15. The process according to claim 11 wherein said hydrocarbons comprise pentenes and pentanes.

16. The process according to claim 11 wherein said hydrocarbons comprise hexenes and hexanes.

17. The process according to claim 1 comprising:

contacting a feed comprising hydrocarbons having 2 to 9 carbon atoms and containing at least one olefin and a paraffin having the same number of carbon atoms with the aqueous slurry comprising silver nitrate and nitric acid in the absence of silver permanganate, ozone and $H_2O_2$, forming water soluble complexes of silver and olefin, removing said aqueous solution containing said silver complexes from contact with said hydrocarbons, decomposing said silver complexes and separating said olefin as separated olefins.

18. The process according to claim 17 wherein said contacting is by countercurrent flow.

19. The process according to claim 18 wherein said contacting is carried out at a temperature in the range of 0 to 120° F.

20. The process according to claim 19 wherein said decomposing is carried out by heating the aqueous solution containing said silver complexes at a temperature in the range of 140 to 220° F.

21. The process according to claim 17 comprising:

contacting said recovered olefins with an aqueous solution comprising silver nitrate and nitric acid, forming water soluble complexes of silver and olefin, removing said aqueous solution containing said silver complexes from contact with said recovered olefin, decomposing said silver complexes and recovering said olefin.

22. The process according to claim 5, 6, 9 or 17 carried out in the presence of acetylenes without the formation of silver acetylides.

23. The process according to claim 5, 6, 9 or 17 carried out in the presence of hydrogen without the formation of reduced silver metal.

24. The process according to claim 1, 7 or 17 carried out in the presence of silver nitrate in excess of the solubility of silver nitrate in the water present.

25. A process comprising contacting an aqueous solution of a silver salt and nitric acid with an organic feed containing at least one compound containing an olefinic unsaturation having a first concentration under conditions of temperature and pressure to form a complex of said silver and said compound containing said olefinic unsaturation, wherein said silver salt is present in the aqueous solution in excess of its solubility as finely divided solid particles transported as a slurry.

26. The process according to claim 25 wherein said organic feed comprises hydrocarbons having 2 to 9 carbon atoms.

27. The process according to claim 25 wherein said organic feed comprises hydrocarbons having 2 to 6 carbon atoms.

28. The process according to claim 26 wherein said hydrocarbons comprise olefins and paraffins of the same number of carbon atoms.

29. The process according to claim 26 wherein said complex of said silver salt and compound containing olefinic unsaturation is separated from said organic feed and decomposed to recover said compound having olefinic unsaturation in a second concentration greater than said first concentration.

30. The process according to claim 25 wherein said silver salt is silver nitrate.

31. The process according to claim 25 comprising:

contacting a feed comprising hydrocarbons having 2 to 9 carbon atoms and containing at least one olefin with the aqueous solution comprising silver nitrate and nitric acid, forming water soluble complexes of silver and olefin, removing said aqueous solution containing said silver complexes from contact with said hydrocarbons, decomposing said silver complexes and recovering said olefin.

32. The process according to claim 31 wherein nitric acid is present in the range of 0.5 to 10 wt. % of said solution.

33. The process according to claim 31 wherein said hydrocarbons comprise a mixture of olefins and paraffins having varying numbers of carbon atoms.

34. The process according to claim 31 wherein said olefins have varying numbers of carbon atoms.

35. The process according to claim 31 wherein hydrocarbons comprise olefins and paraffins having the same number of carbon atoms.

36. The process according to claim 35 wherein said hydrocarbons comprise ethylene and ethane.

37. The process according to claim 35 wherein said hydrocarbons comprise propylene and propane.

38. The process according to claim 35 wherein said hydrocarbons comprise butylenes and butanes.

39. The process according to claim 35 wherein said hydrocarbons comprise pentenes and pentanes.

40. The process according to claim 35 wherein said hydrocarbons comprise hexenes and hexanes.

41. The process according to claim 25 comprising:

contacting a feed comprising hydrocarbons having 2 to 9 carbon atoms and containing at least one olefin and a paraffin having the same number of carbon atoms with the aqueous solution comprising silver nitrate and nitric acid in the absence of silver permanganate, ozone and $H_2O_2$, forming water soluble complexes of silver and olefin, removing said aqueous solution containing said silver complexes from contact with said hydrocarbons, decomposing said silver complexes and separating said olefin as separated olefins.

42. The process according to claim 41 wherein said contacting is by countercurrent flow.

43. The process according to claim 42 wherein said contacting is carried out at a temperature in the range of 0 to 120° F.

44. The process according to claim 43 wherein said decomposing is carried out by heating the aqueous solution containing said silver complexes at a temperature in the range of 140 to 220° F.

45. The process according to claim 41 comprising:

contacting said recovered olefins with an aqueous solution comprising silver nitrate and nitric acid, forming water soluble complexes of silver and olefin, removing said aqueous solution containing said silver complexes from contact with said recovered olefin, decomposing said silver complexes and recovering said olefin.

46. The process according to claim 30, 25, 31 or 41 carried out in the presence of acetylenes without the formation of silver acetylides.

47. The process according to claim 30, 25, 31, or 41 carried out in the presence of hydrogen without the formation of reduced silver metal.

48. The process of claim 1 wherein the concentration of nitric acid is from 0.1 to 2.0 normal.

49. The process of claim 1 wherein the concentration of nitric acid is from 0.5 to 1.0 normal.

* * * * *